US012296183B2

(12) United States Patent
Mueller et al.

(10) Patent No.: US 12,296,183 B2
(45) Date of Patent: May 13, 2025

(54) ACOUSTIC POWER TRANSFER FOR IMPLANTABLE MEDICAL DEVICE

(71) Applicant: Medtronic, Inc., Minneapolis, MN (US)

(72) Inventors: Jerel Mueller, St. Paul, MN (US); Sarah Offutt, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 701 days.

(21) Appl. No.: 17/598,642

(22) PCT Filed: Apr. 23, 2020

(86) PCT No.: PCT/US2020/029606
§ 371 (c)(1),
(2) Date: Sep. 27, 2021

(87) PCT Pub. No.: WO2020/219738
PCT Pub. Date: Oct. 29, 2020

(65) Prior Publication Data
US 2022/0161037 A1    May 26, 2022

Related U.S. Application Data

(60) Provisional application No. 62/838,787, filed on Apr. 25, 2019.

(51) Int. Cl.
*A61N 1/378* (2006.01)
*A61N 1/36* (2006.01)
(Continued)

(52) U.S. Cl.
CPC ....... *A61N 1/3787* (2013.01); *A61N 1/36007* (2013.01); *A61N 1/3605* (2013.01);
(Continued)

(58) Field of Classification Search
CPC ............. A61N 1/3787; A61N 1/36007; A61N 1/3605; A61N 1/3758; A61N 1/375; H02J 50/15; H02J 2310/23
See application file for complete search history.

(56) References Cited

U.S. PATENT DOCUMENTS

| 9,731,138 B1 | 8/2017 | Stadler et al. |
| 2006/0136004 A1* | 6/2006 | Cowan ................. A61N 1/3621 607/33 |

(Continued)

FOREIGN PATENT DOCUMENTS

WO    WO 2020/219738 A1    10/2020

OTHER PUBLICATIONS

International Search Report and Written Opinion from PCT Application PCT/US2020/029606 dated Jul. 10, 2020, 19 pgs.

*Primary Examiner* — Eugene T Wu
(74) *Attorney, Agent, or Firm* — Husch Blackwell LLP (57) ABSTRACT

The present disclosure is directed to an implantable medical device including a housing having a generally planar portion, and a piezoelectric transducer disposed within the housing, wherein a receiving face of the piezoelectric transducer is arranged at an oblique angle with respect to a poling axis of the piezoelectric transducer, and an electrode to deliver a neurostimulation therapy. The implantable medical device is configured to receive energy signals from an external device and transduce the received energy signals into electrical power.

11 Claims, 10 Drawing Sheets

(51) Int. Cl.
*A61N 1/375* (2006.01)
*H02J 50/15* (2016.01)
(52) U.S. Cl.
CPC ............ *A61N 1/3758* (2013.01); *H02J 50/15* (2016.02); *H02J 2310/23* (2020.01)

(56) References Cited

U.S. PATENT DOCUMENTS

| | | | |
|---|---|---|---|
| 2007/0293895 A1* | 12/2007 | Cowan | A61N 1/3968 607/5 |
| 2008/0103558 A1* | 5/2008 | Wenzel | A61N 1/3787 607/61 |
| 2008/0312720 A1* | 12/2008 | Tran | A61N 1/37217 607/61 |
| 2017/0108926 A1 | 4/2017 | Moon et al. | |
| 2018/0256905 A1 | 9/2018 | Francia et al. | |
| 2019/0199139 A1* | 6/2019 | Perry | H02J 50/30 |
| 2021/0297795 A1* | 9/2021 | Vermeiren | H04R 25/65 |

\* cited by examiner

ACOUSTIC POWER TRANSFER FOR IMPLANTABLE MEDICAL DEVICE

CROSS-REFERENCE TO RELATED APPLICATIONS

This application claims the benefit of U.S. Provisional Patent Application No. 62/838,787, filed Apr. 25, 2019, the entire contents of which is hereby incorporated by reference.

FIELD

The present technology generally relates to medical devices and, more particularly, to systems for acoustic power transfer to an implanted medical device.

BACKGROUND

Medical devices, including implantable medical devices (IMDs), may be used to treat a variety of medical conditions. Medical electrical stimulation devices, for example, may deliver electrical stimulation therapy to a patient via external or implanted electrodes. Electrical stimulation therapy may include stimulation of nerve tissue, muscle tissue, the brain, the heart, or other tissue within a patient. In some examples, an electrical stimulation device is fully implanted within the patient. For instance, an implantable electrical stimulation device may include a power source, an implantable electrical stimulation generator, and one or more implantable electrodes. In some examples, an electrical stimulation system may include some components implantable within the patient and some components external to the patient.

Medical electrical stimulators have been proposed for use to relieve a variety of symptoms or conditions such as chronic pain, tremor, Parkinson's disease, depression, epilepsy, migraines, urinary or fecal incontinence, pelvic pain, sexual dysfunction, obesity, overactive bladder and gastroparesis. An electrical stimulator may be configured to deliver electrical stimulation therapy via electrodes implantable proximate to the spinal cord, gastrointestinal organs, tibial nerve, sacral nerve, peripheral nerves, or within the brain of a patient.

Some IMDs rely on batteries for an energy source, such as conventional batteries intended to last the lifetime of the IMD. However when a conventional battery depletes, the entire IMD must be explanted and replaced. Other IMDs include rechargeable batteries which can be recharged as needed by the patient or a clinician. Some IMDs rely on transcutaneous power transmission from an external device to power the IMD in whole or in part to cause electrical stimulation therapy to be delivered.

SUMMARY

The techniques of the present disclosure generally relate to an implantable medical electrical stimulation device having an array of piezoelectric transducers where at least two receiving faces of the array of piezoelectric transducers are positioned in an oblique angle to one another to enable the receipt of ultrasonic waves for the recharging of a rechargeable battery across a wide range of angles. For example, in some embodiments, the implantable medical electrical stimulation device can include a domed protrusion configured focus transmitted ultrasonic waves towards the receiving faces of one or more piezoelectric transducers to enable receipt of transmitted ultrasonic waves across a wide range of angles. In some embodiments, the receiving faces of the array of piezoelectric transducers can be covered in a domed epoxy layer and biocompatible titanium casing layer configured to focus transmitted ultrasonic waves towards the receiving faces of the array of piezoelectric transducers, thereby enabling the receipt of transmitted ultrasonic waves across a range of about 40 degrees relative to a central poling axis of the array of the piezoelectric transducers.

One embodiment of the present disclosure provides an implantable medical electrical stimulation device, including an electrical stimulation therapy circuit, a rechargeable battery, and an array of piezoelectric transducers. The electrical stimulation therapy circuit can be operably coupled to one or more electrodes configured to deliver electrical stimulation therapy. The rechargeable battery can be configured to power the electrical stimulation therapy circuit. The array of piezoelectric transducers, each of which can include a receiving face, can be configured to received transmitted ultrasonic waves convertible to source of electrical energy for selective recharging of the rechargeable battery. The array of piezoelectric transducers can be arranged such that at least two of the receiving faces are positioned at an oblique angle to one another to enable receipt of transmitted ultrasonic waves across a wide range of angles.

In one embodiment, the array of piezoelectric transducers can be configured to receive transmitted ultrasonic waves across a range of about 40 degrees relative to a central poling axis of the array of the piezoelectric transducers. In one embodiment, the array of piezoelectric transducers can be configured to receive transmitted ultrasonic waves in a frequency range of between about 100 kHz and about 5 MHz. In one embodiment, the implantable medical electrical stimulation device can further include a feedback coil configured to generate an indication level of regenerative electrical power received from transmitted ultrasonic waves.

In one embodiment, at least two of the receiving faces are offset about 15 degrees relative to one another. In one embodiment, the array of piezoelectric transducers can include a central transducer having a receiving face positioned substantially orthogonal to a central poling axis, and a plurality of peripheral transducers, each having a receiving face offset about 15 degrees relative to the receiving face of the central transducer. In one embodiment, the receiving faces of the array of piezoelectric transducers can be covered in an epoxy layer. In one embodiment, the receiving faces of the array of piezoelectric transducers can be covered in a biocompatible titanium casing. In one embodiment, the biocompatible titanium casing can include a domed protrusion configured focus transmitted ultrasonic waves towards the receiving faces of the array of piezoelectric transducers.

Another embodiment of the present disclosure provides an implantable medical electrical stimulation device, including a biocompatible titanium casing, an electrical stimulation therapy circuit, a rechargeable battery, and one or more piezoelectric transducers. The electrical stimulation therapy circuit can be housed within the biocompatible casing and candy configured to deliver electrical stimulation therapy. The rechargeable battery can be configured to power the electrical stimulation therapy circuit. The one or more piezoelectric transducers, each of which can include a receiving face, can be configured to received transmitted ultrasonic waves convertible to source of electrical energy for selective recharging of the rechargeable battery. The biocompatible casing can include a domed protrusion configured focus transmitted ultrasonic waves towards the receiving faces of the one or more piezoelectric transducers to enable receipt of transmitted ultrasonic waves across a wide range of angles.

In one embodiment, the one or more piezoelectric transducers can be configured to receive transmitted ultrasonic waves across a range of about 40 degrees relative to a central poling axis of the array of piezoelectric transducers. In one embodiment, the implantable medical electrical stimulation device can further include a feedback coil configured to generate an indication level of regenerative electrical power received from transmitted ultrasonic waves. In one embodiment, at least one piezoelectric transducer of the one or more piezoelectric transducers can include a domed receiving face. In one embodiment, a receiving face of the one or more piezoelectric transducers can be covered in an epoxy layer.

Another embodiment of the present disclosure provides an implantable medical electrical stimulation device, including an electrical stimulation therapy circuit, a rechargeable battery, and array of piezoelectric electric transducers, and a feedback coil. The electrical stimulation therapy circuit can be operably coupled to one or more electrodes configured to deliver electrical stimulation therapy. The rechargeable battery can be configured to power the electrical stimulation therapy circuit. The array of piezoelectric transducers can each include a receiving face configured to receive transmitted ultrasonic waves in a frequency range of between about 100 kHz and about 5 MHz, which can be convertible to source of electrical energy for selective recharging of the rechargeable battery. The feedback coil can be configured to generate an indication level of regenerative electrical power received from transmitted ultrasonic waves. Further, the array of piezoelectric transducers can include at least one transducer having a receiving face oriented at an oblique angle with respect to a poling axis of the transducer. The receiving faces of the array of piezoelectric transducers can be covered in a domed epoxy layer and biocompatible titanium casing layer configured to focus transmitted ultrasonic waves towards the receiving faces of the array of piezoelectric transducers. The array of piezoelectric transducers can be configured to receive transmitted ultrasonic waves across a range of about 40 degrees relative to a central poling axis of the array of the piezoelectric transducers. The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
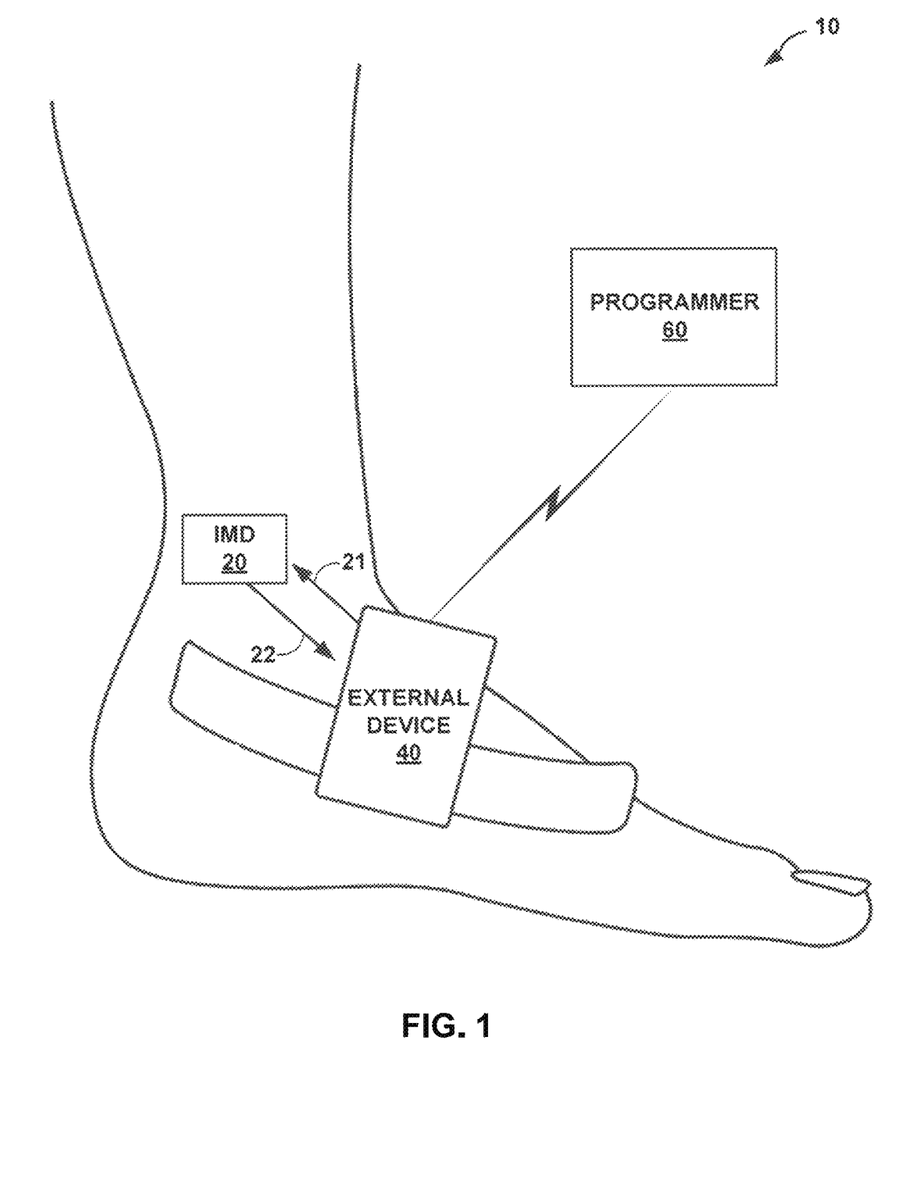
FIG. 1 is a schematic diagram of a minimally invasive system capable of delivering a neurostimulation therapy, in accordance with one or more techniques of this disclosure.

FIG. 1 is a schematic diagram of a minimally invasive system 10 capable of delivering a neurostimulation therapy, in accordance with one or more techniques of this disclosure. Example system 10 includes an implantable medical device (IMD) 20, an external device 40, and an optional programming device 60.

IMD 20 includes electronic circuitry, e.g., comprising one or more electronic circuits for delivering electrical stimulation therapy, enclosed in a sealed housing and coupled to one or more therapy delivery electrodes. IMD 20 may collect (e.g., harvest) energy signals 21 from external device 40 and transduce the collected energy signals 21 into electrical power. In one example, IMD 20 may be configured to receive energy signals and transduce the received energy signals into electrical power that is used to deliver electrical stimulation therapy. In another example, IMD 20 may be configured as to receive energy signals and transduce the received energy signals into electrical power that is used to recharge a battery of IMD 20.

External device 40 may be a handheld device, or a wearable device including a strap 42 or other attachment member(s) (e.g., adhesive) for securing external device 40 to the patient in operable proximity to IMD 20. In some examples, external device 40 may be a patch worn by the patient. External device 40 may output energy signals 21 for receipt by IMD 20, for example ultrasonic waves. Suitable frequencies of energy signals 21 may be in the range of 500 kHz to 1 MHz, or in the range of 100 kHz to 5 MHz. In an example, IMD 20 may output a feedback signal 22.

The use of ultrasound for wireless power transfer offers some advantages over other power transfer techniques. The wavelength of ultrasound within tissue is on the order of millimeters, which facilitates an efficient harvesting of power for smaller miniaturized implants as well. Body tissue absorption of ultrasound is lower than other power transfer techniques, resulting in less heating of tissue near the implant and more energy delivered to the implant. Low tissue absorption also allows a higher power intensity threshold for safe operation. Further, ultrasound does not generate significant heat within a titanium housing of an IMD.

External device 40 may be a battery powered device including a transmitter used to transcutaneously transmit energy signals 21 to a receiver included in IMD 20. External device 40 may include one or more primary or rechargeable cells and therefore may include a power adaptor and plug for re-charging in a standard 110V or 220V wall outlet, for example.

In an example wherein IMD 20 may be configured to receive energy signals and transduce the received energy signals into electrical power that is used to deliver electrical stimulation therapy, system 10 may include a programmer 60 configured to program external device 40 for operation to cause delivery of therapy to the patient. For example, programmer 60 may be configured to program one or more of the following parameters of external device 40: pulse amplitude, pulse width, pulse shape, pulse frequency, duty cycle, and therapy on and off times. External device 40 may use the parameters to generate energy signals that will cause IMD 20 to deliver stimulation with the desired attributes (e.g., pulse amplitude, pulse width, pulse shape, pulse frequency, duty cycle, and therapy on and off times). In some examples, programmer 60 may be a clinician programmer that may be able to program all of the parameters of external device 40. In some examples, programmer 60 may be a patient programmer that may be able to program a subset of the parameters of external device 40.

It is contemplated that in some examples the functionality required for transmitting power to IMD 20 and for controlling therapy delivery may be implemented in a single external device. For example, power transmission capability of external device 40 and programming capabilities of programmer 60 may be combined in a single external device, which may be a handheld or wearable device.

The depiction in FIG. 1 is merely illustrative. In actual use, external device 40 would be positioned as near as possible to IMD 20.

Figure 2:
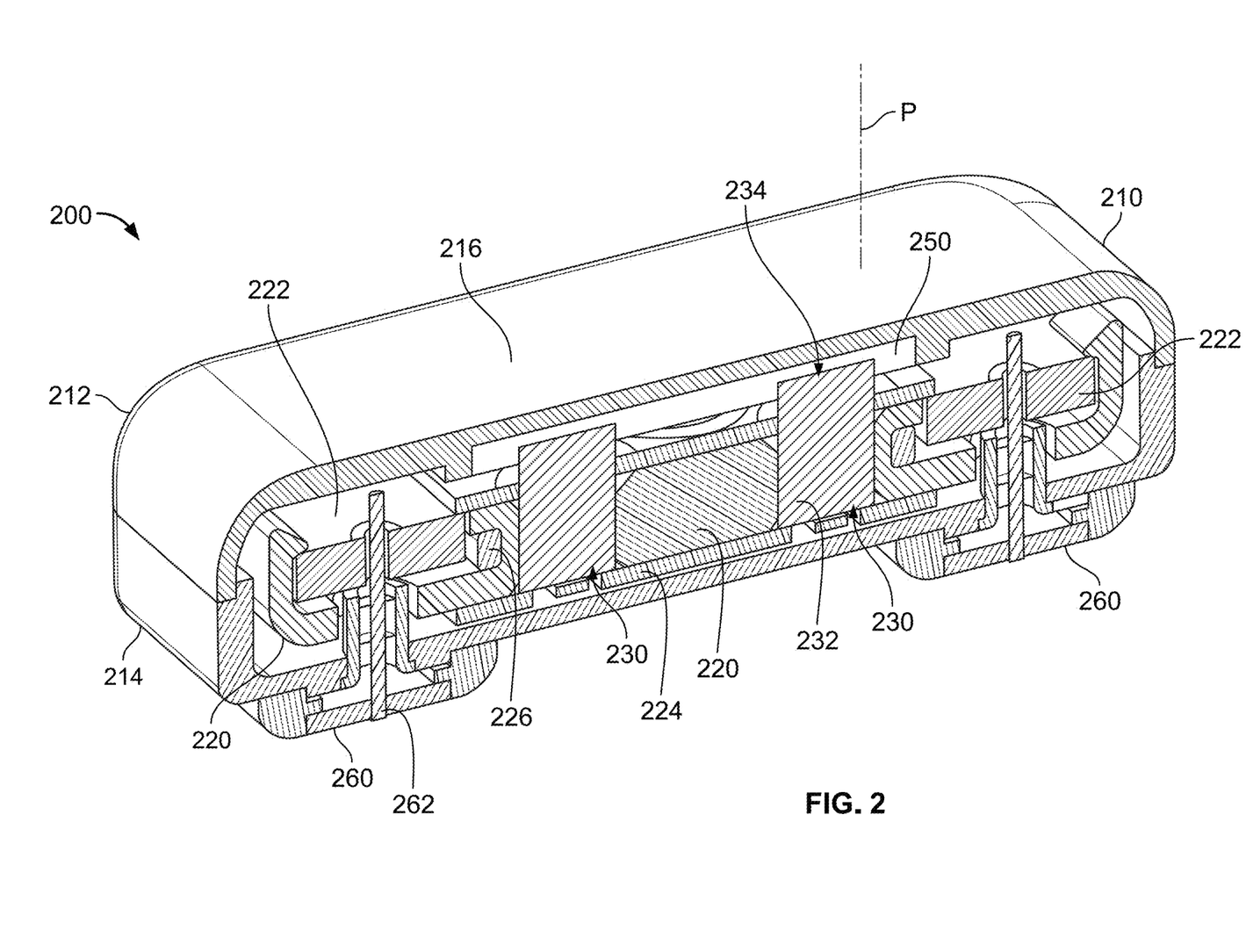
FIG. 2 is a cross sectional view of an IMD according to an embodiment of the disclosure.

Referring now to FIG. 2, an IMD 200 is depicted having a housing 210. Housing 210 may be constructed from any suitable material. In one example, housing 210 may be constructed from titanium. Housing 210 includes a first portion 212 and a second portion 214, joined together by welding or other suitable techniques such that housing 210 is hermetically sealed.

Housing 210 includes electronic circuitry and associated components disposed therein. A chassis or board 220 provides a mounting location for circuit board 222, flexible interconnects 224, a feedback coil 226 and one or more energy receivers 230. In an example, one or more batteries and associated charging circuitry (not depicted) are also included. Feedback coil 226 may generate or transmit a signal to external device 40 that represents an indication of one or more parameters of IMD 200. For example, feedback coil may generate or transmit an indication of the level of electrical power transduced from energy signals 21, an indication of the level of electrical stimulation being delivered by IMD 200, or other parameters.

In an example, energy receiver 230 may be a piezoelectric transducer. Piezoelectricity is the accumulation of electric charge in response to a mechanical stress and may manifest in a converse manner as well (i.e. mechanical stress in response to an electric charge). Two common piezoelectric materials include ceramics and crystals, such as lead zirconate titanate (PZT) ceramic and quartz crystal. Piezoelectric transducer 230 is configured to accumulate electrical charge in response to mechanical stress from ultrasonic waves 21 from external device 40.

As depicted in FIG. 2, IMD 200 includes a plurality of piezoelectric transducers 230, each including a body portion 232, a receiving face 234, and a poling axis P. For simplicity poling axis P is only depicted for a single transducer in each drawing, although it will be understood that each transducer includes a unique poling axis. An epoxy layer 250 is included to provide mechanical coupling between piezoelectric transducers 230 and housing 210, and eliminate any air bubbles that could reflect ultrasonic waves 21. In an example, epoxy 250 may serve as an impedance matching layer from housing 210 to piezoelectric transducer 230.

Piezoelectric transducers 230 are sensitive to orientation with respect to delivered ultrasonic waves 21. In the embodiment depicted in FIG. 2, receiving face 234 is oriented generally orthogonal to poling axis P, and ultrasonic waves 21 are intended to be delivered in a direction along or close to the poling axis P so as to transmit to receiving face 234 in a direction along or close to the poling axis P as well. Thus, to minimize the effects of refraction of ultrasonic waves 21, the poling axes P of the piezoelectric transducers 230 are arranged to be orthogonal to a generally planar portion 216 of housing 210. In the embodiment of FIG. 2, receiving faces 234 are generally aligned parallel with the generally planar portion 216.

In general, increasing the area of receiving face 234 increases the amount of power piezoelectric transducer 230 can harvest from ultrasonic waves 21. Once the piezoelectric transducer 230 is placed inside a titanium housing 210 together with epoxy 250 for mechanical coupling, the generalization still holds but can become more complex as the total IMD 200 may become a resonant chamber for acoustic waves.

IMD 200 further includes one or more electrodes 260. Electrodes 260 may be located on a housing of IMD 20, on one or more leads connected to the housing of IMD 20, or a combination. Electrodes 260 may be any suitable type of electrode, including but not limited to, pad electrodes, ring electrodes, paddle electrodes, or any other type of electrode capable of delivering electrical stimulation to a patient. In one example, one or more electrodes 260 may include a corkscrew or tined element for fixation of IMD 200 to a patient. Each electrode 260 is electrically connected to circuit board 222 by way of a feedthrough 262 which is configured to maintain the hermetic seal of housing 210.

IMD 200 is configured to be implanted such that one or more electrodes 260 are in contact with or proximate relation to a target nerve, and such that generally planar portion 216 of housing 210 is oriented to allow for suitable energy harvesting from external device 40.

Although not depicted in FIG. 2, IMD 200 may include one or more fixation elements or features such as suture tabs, tines, barbs, or other suitable passive or active fixation elements as known in the art.

Referring now generally to FIGS. 3-6, embodiments are depicted and described of piezoelectric transducers and arrays of transducers having improved wider angles of acceptance as compared to an embodiment such as depicted in FIG. 2. The embodiments of FIGS. 3-6 have many similarities to IMD 200 and for simplicity the description of common components is not repeated in the following, and like numerals may designate like parts throughout that are corresponding or analogous.

Piezoelectric transducers exhibit a sensitivity to the angle of propogation for incoming ultrasonic waves that the piezoelectric transducer is able to effectively harvest. This is formalized as an acceptance angle, where incoming ultrasonic waves traveling at an angle greater than the critical acceptance angle results in total reflection of the ultrasonic wave. Thus an angle between the transmitter of external device 40 and a poling axis of the piezoelectric transducer may reduce the effectiveness of energy transfer, with greater angles potentially resulting in little to no energy transfer. Further, refraction of the ultrasonic waves through changing materials of titanium housing, epoxy and piezoelectric transducer may additionally reduce the effectiveness of angled transmission of ultrasonic waves.

Misalignment between the external device 40 and an IMD 20 creating an angled transmission of ultrasonic waves may be caused by improper positioning of the external device, migration of the IMD, or other factors. For example, if a user of external device 40 does not have external device 40 properly positioned over the implant location of IMD 20. More problematic is migration of the IMD. IMDs implanted within patients sometimes undesirably shift, rotate or otherwise move from an intended implant location or orientation. This phenomenon is referred to as migration. Migration may take the form of translation, rotation about one or more of the axes of the IMD, a combination thereof or other movement. Migration may be caused by physiological changes to the patient, an impact to the patient in the area the IMD is implanted, a loosening or deterioration of a fixation means of the IMD, or other reasons.

While it may be possible to at least partially compensate for some instances of IMD migration by correspondingly repositioning the external device, other instances of migration may be severe enough that sufficient energy transfer is no longer possible to suitably operate the IMD, resulting in an undesirable surgical procedure to reposition or replace the IMD.

The embodiments depicted in FIGS. 3-6 include one or more piezoelectric transducers machined, formed, arranged or configured so as to be more accepting of incoming ultrasonic waves from a variety of angles, thereby providing a wider angle of acceptance for the IMD.

Figure 3:
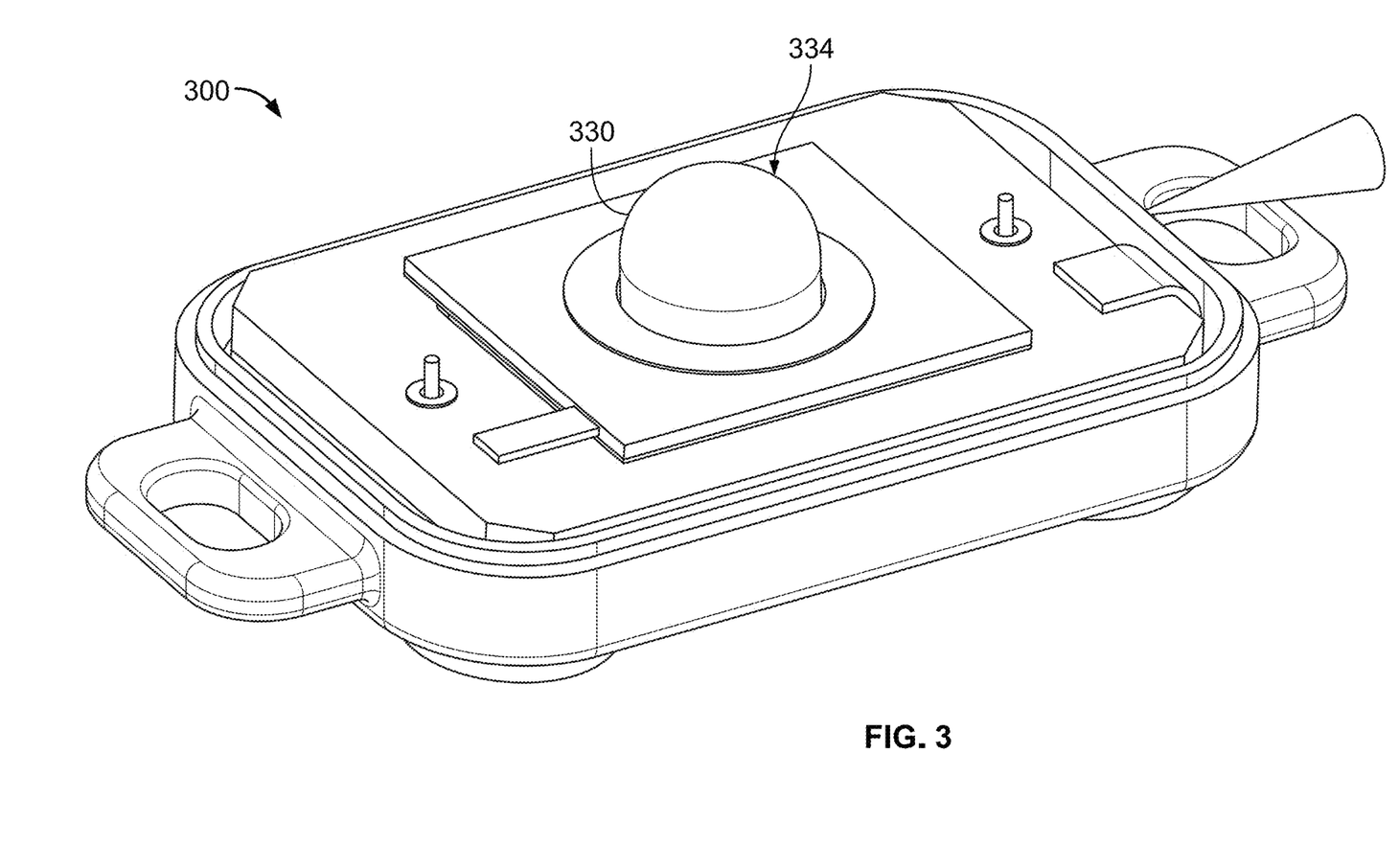
FIG. 3 is a perspective view of an IMD according to another embodiment of the disclosure.
Figure 3A:
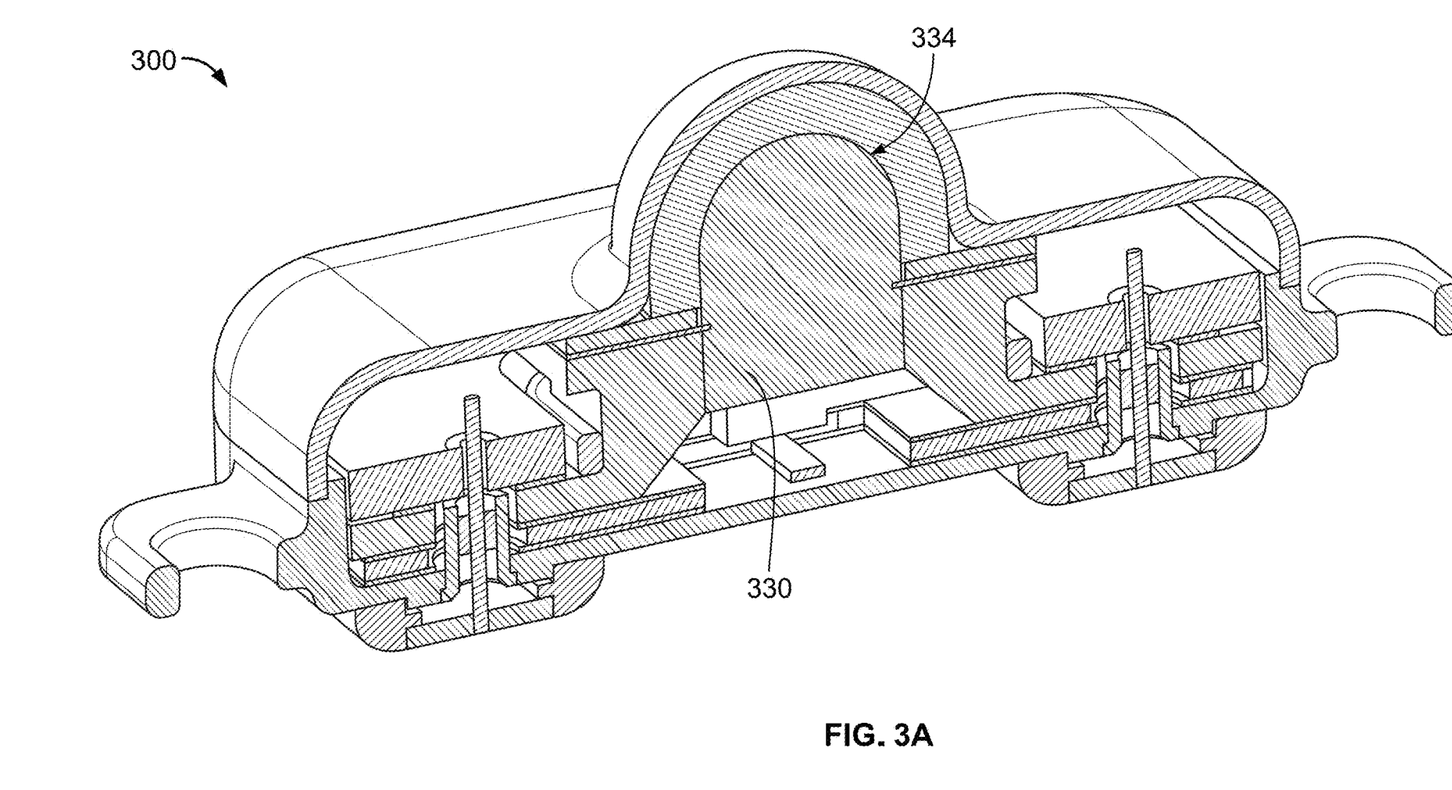
FIG. 3A is a cross sectional view of the IMD of FIG. 3.

Referring now to FIGS. 3-3A, an IMD 300 is depicted having a piezoelectric transducer 330 with a domed receiving surface 334. For clarity, IMD 300 is depicted in FIG. 3 with a first housing portion removed. Domed receiving surface 330 presents a normal path for incoming ultrasonic waves across a wide range of angles.

Experiments were conducted by the Applicant on the effect of power transfer to a domed piezoelectric transducer covered in epoxy and a titanium layer, similar to the arrangement depicted in FIGS. 3-3A. Results of the experiments indicated that approximately twenty degrees represents an angle at which further angled ultrasonic wave transmission resulted in little to no power transfer to the piezoelectric transducer. Comparatively, experiments were also conducted by the Applicant using a single piezoelectric transducer similar to the arrangement depicted in FIG. 2, which exhibited an acceptance angle of approximately ten degrees. Thus the domed piezoelectric transducer represents an approximately twofold increase in acceptance angle.

Although IMD 300 is depicted with only a single piezoelectric transducer 330 with a domed receiving surface 334, multiple such piezoelectric transducers could be arranged in an array as part of IMD 300.

Figure 4:
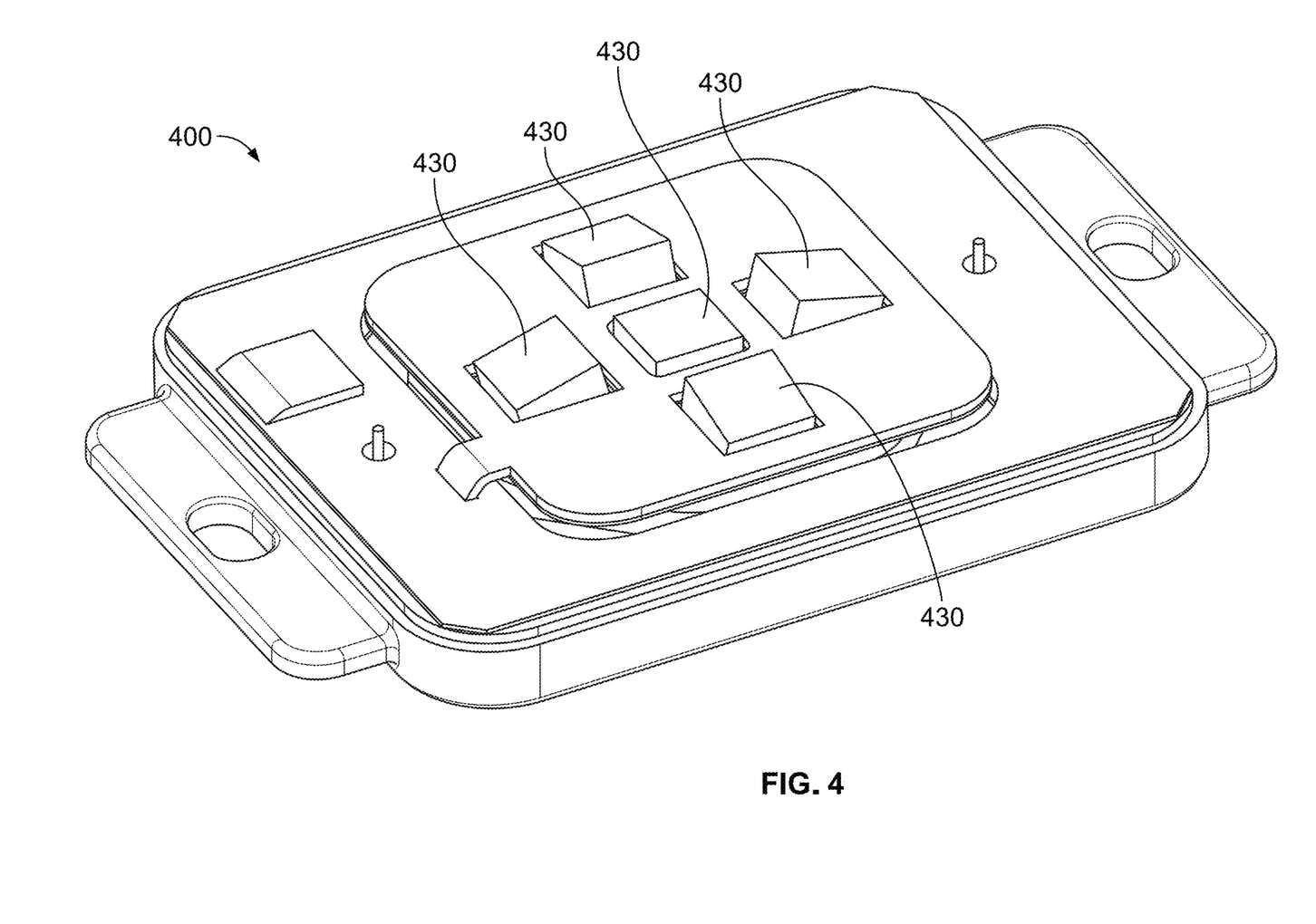
FIG. 4 is a perspective view of an IMD according to another embodiment of the disclosure.
Figure 4A:
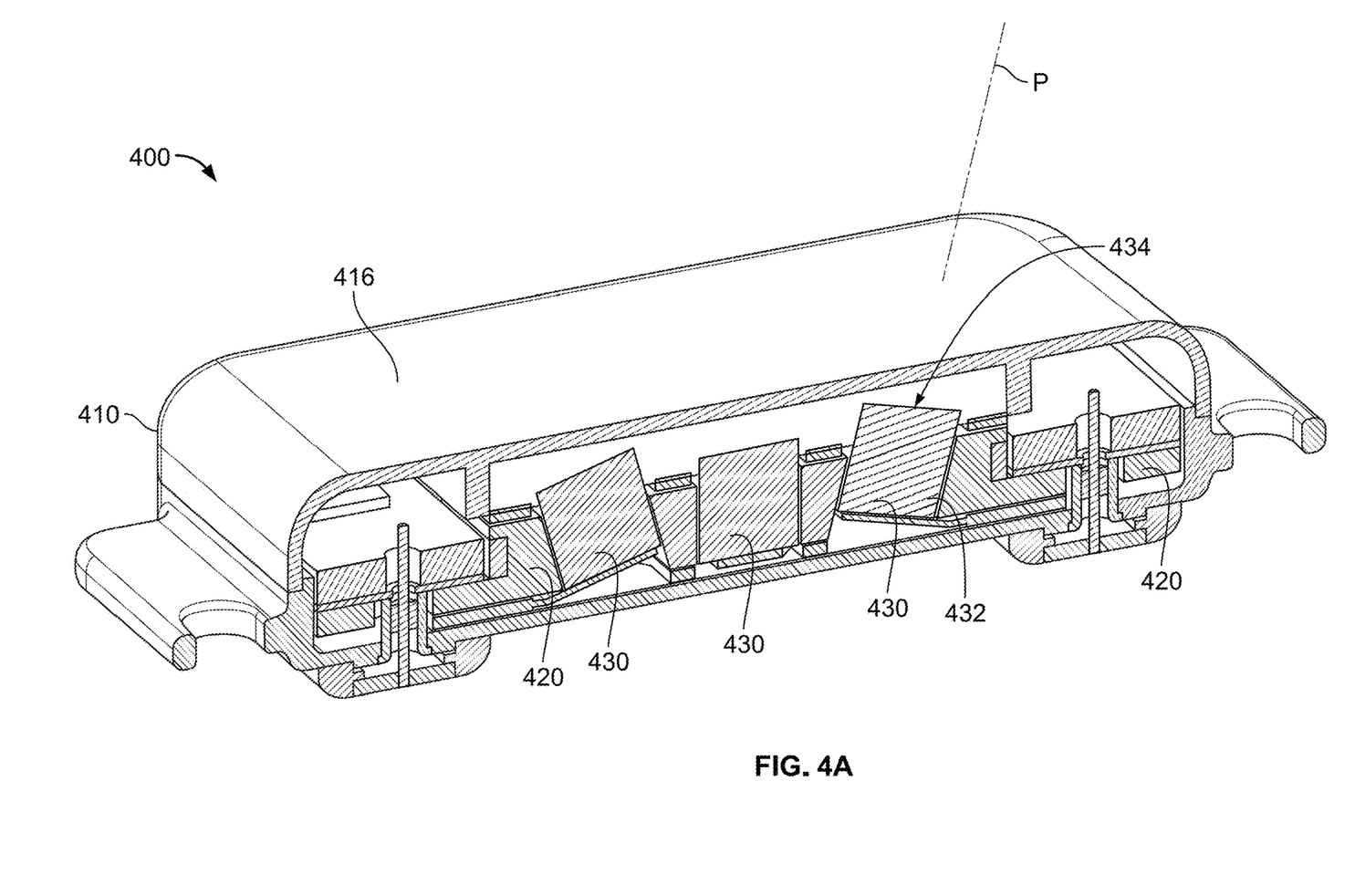
FIG. 4A is a cross sectional view of the IMD of FIG. 4.

Referring now to FIGS. 4-4A, an IMD 400 is depicted having an array of piezoelectric transducers 430. The receiving faces 434 of piezoelectric transducers 430 are oriented orthogonal to respective body portions 432 and poling axis P, but body portions 432 of some piezoelectric transducers 430 are disposed in chassis 420 at an angle such that respective receiving faces 434 are at an oblique angle to a generally planar portion 416 of housing 410. The various piezoelectric transducers 430 may be disposed in chassis 420 at similar, or different angles. Piezoelectric transducers 430 may also be arranged such that one or more receiving faces 434 are angled with respect to one or more other receiving faces 434. Piezoelectric transducers 430 may also be angled about more than one axis. IMD 400 thereby provides a wider range of acceptance angles for the device as a whole, wherein one or more piezoelectric transducers 430 may be aligned at an unsuitable angle to harvest energy from an ultrasonic wave yet other piezoelectric transducers 430 are aligned at suitable angles for harvesting.

Experiments were conducted by Applicant on the effect of power transfer to an array of piezoelectric transducers angled approximately fifteen degrees relative to one another and covered in epoxy and a titanium layer, similar to the arrangement depicted in FIGS. 4-4A. Results of the experiments indicated that such an arrangement yielded an acceptance angle greater than forty degrees from the normal of the generally planar portion 416 of housing 410, with energy transfers of greater than thirty percent efficient compared to energy transfer with ultrasonic waves traveling along the normal of the generally portion 416.

Figure 5:
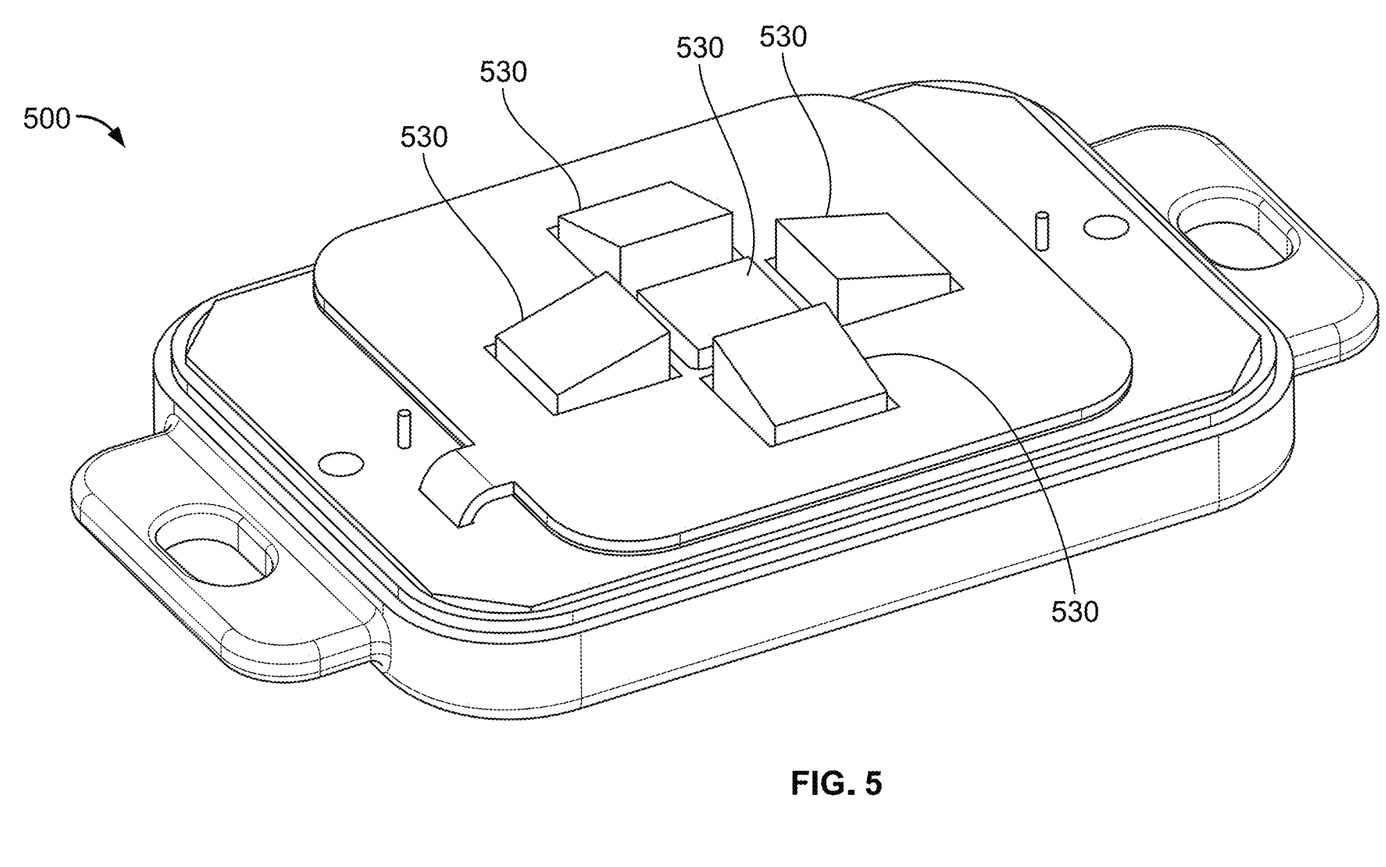
FIG. 5 is a perspective view of an IMD according to another embodiment of the disclosure.
Figure 5A:
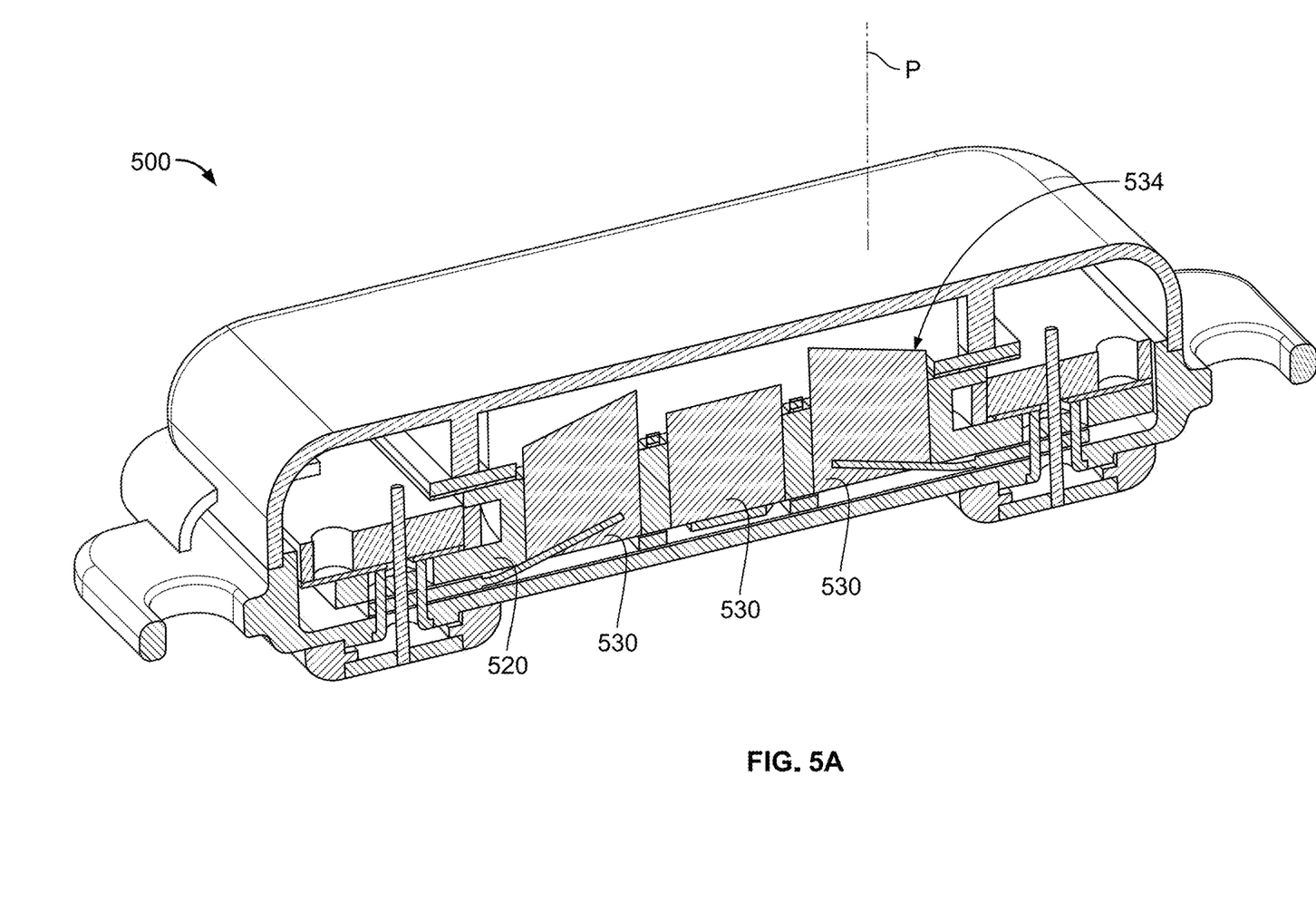
FIG. 5A is a cross sectional view of the IMD of FIG. 5.

Referring now to FIGS. 5-5A, an IMD 500 is depicted having an array of piezoelectric transducers 530. The receiving faces 534 of some of the piezoelectric transducers 530 have been machined or otherwise formed so as to be oriented at an oblique angle (not orthogonal) to respective poling axis P. The various piezoelectric transducers 530 may be disposed in chassis 520 at similar, or different angles. Piezoelectric transducers 530 may also be arranged such that one or more receiving faces 534 are angled with respect to one or more other receiving faces 534. IMD 500 thereby provides a wider range of acceptance angles for the device as a whole, wherein one or more receiving faces 534 of piezoelectric transducers 530 may be aligned at an unsuitable angle to harvest energy from an ultrasonic wave yet other receiving faces 534 of piezoelectric transducers 530 are aligned at suitable angles for harvesting.

Figure 6:
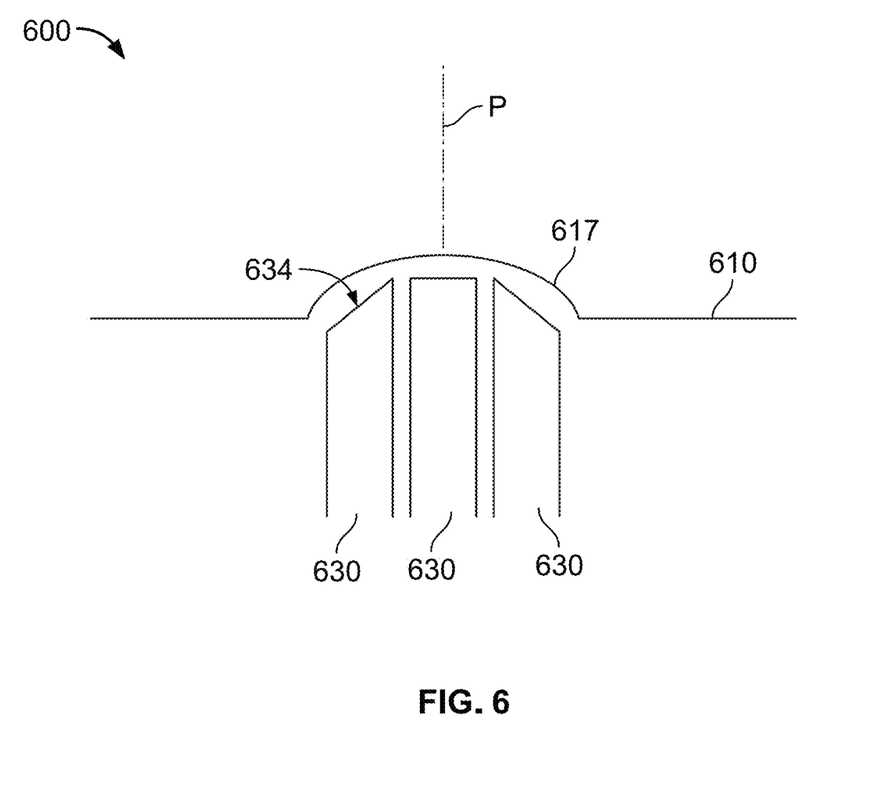
FIG. 6 is an illustration of another embodiment of the disclosure.

Although the embodiments depicted in FIGS. 2-5A include IMD housings generally rectangular and thin in shape with a flat housing profile, other form factors are also contemplated such as circular, oval, square, cylindrical or others. For example, FIG. 6 depicts part of an IMD 600 with a housing 610 having a domed portion 617. An array of piezoelectric transducers 630 are arranged under domed portion 617, the receiving faces 634 of some of the piezoelectric transducers 630 have been machined or otherwise formed so as to be oriented at an oblique angle to respective poling axis P. The profile of domed portion 617 may beneficially refract incoming ultrasonic waves to provide a wider range of acceptance angles for IMD 600.

Figure 7:
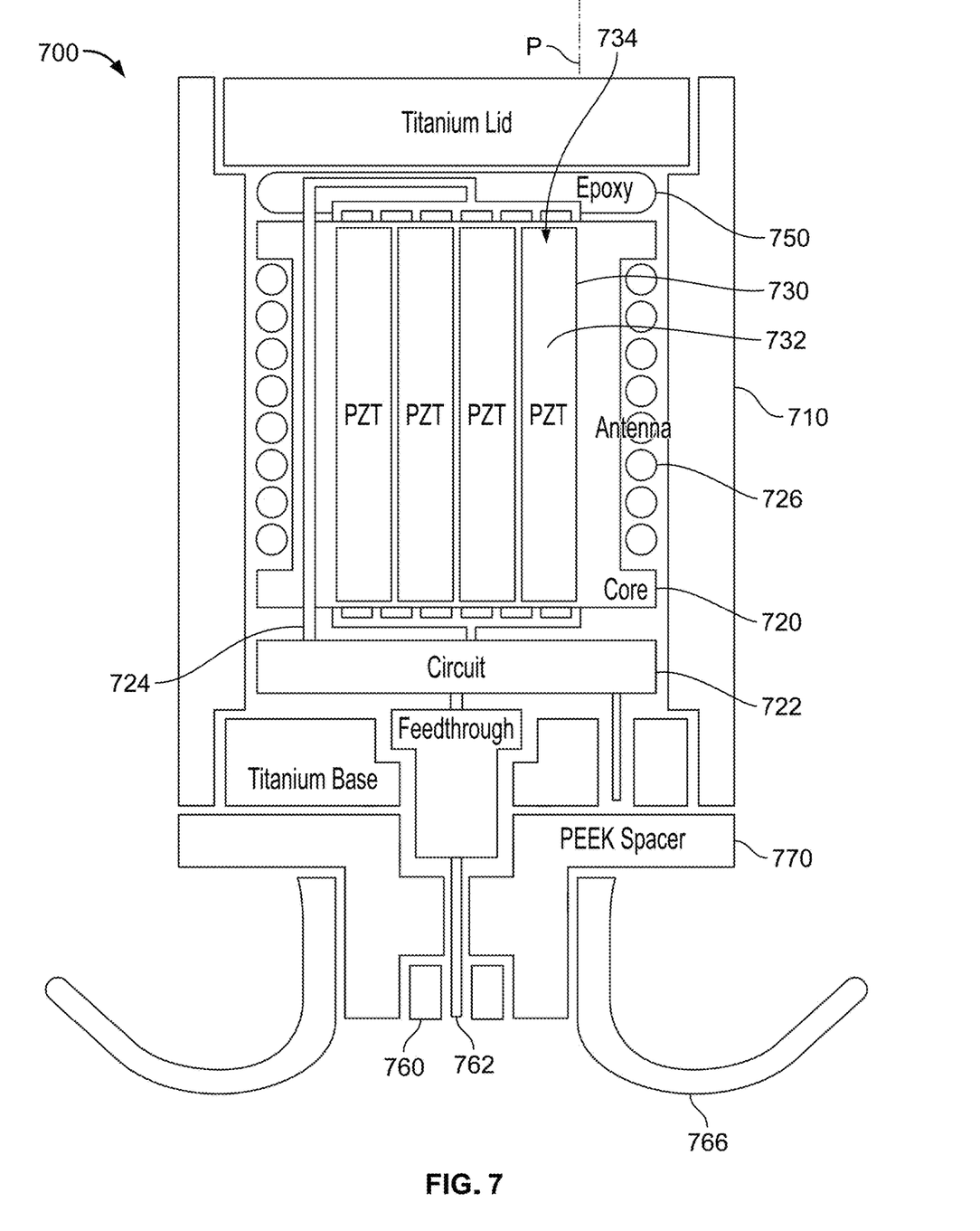
FIG. 7 is a cross sectional view according to another embodiment of the disclosure.

An example of a cylindrical form factor is depicted in FIG. 7. An IMD 700 includes a generally cylindrical housing 710, which in one example may be constructed from titanium. Housing 710 may be constructed from multiple housing portions joined together by welding or other suitable techniques such that housing 710 is hermetically sealed. Housing 710 includes electronic circuitry and associated components disposed therein. A chassis or core 720 provides a mounting location for circuitry 722, flexible interconnects 724, a feedback antenna 726 and one or more piezoelectric transducers 730. In an example, one or more batteries and associated charging circuitry (not depicted) are also included.

Feedback antenna 726 is wrapped around core 720 and may generate or transmit a signal to external device 40 that represents an indication of one or more parameters of IMD 700. For example, feedback coil may generate or transmit an indication of the level of electrical power transduced from energy signals 21, an indication of the level of electrical stimulation being delivered by IMD 700, or other parameters.

Each piezoelectric transducer 730 includes a body portion 732, a receiving face 734, and a poling axis P. An epoxy layer 750 is included to provide mechanical coupling between piezoelectric transducers 730 and housing 710, and eliminate any air bubbles that could reflect ultrasonic waves 21.

IMD 700 further includes at least one electrode 760. As depicted in FIG. 7, electrode 760 is electrically connected to circuitry 722 by way of a feedthrough 762 which is configured to maintain the hermetic seal of housing 710. One or more tines 766 are provided for fixation of IMD 700 to a patient. In an example, tines 766 may be constructed from a shape memory alloy, such as nitinol. Tines 766 are coupled to a spacer 770. In an example, spacer 770 may be constructed from an insulative material such as polyether ether ketone, to isolate housing 710 from tines 766.

Although IMD 700 is depicted in FIG. 7 with a planar outer housing and flat receiving faces 734, variations are contemplated. For example, modifying the housing to have a domed or curved profile, similar to the examples of FIGS. 3A and 6. Or arranging piezoelectric transducers 730 in an angled orientation similar to the example of FIG. 4, or modifying one or more receiving faces 734 to be angled similar to the example of FIG. 5.

Generally, while some examples disclosed herein include piezoelectric receiving faces having a generally planar profile, also contemplated are curved or non-planar receiving faces. Further, aspects of the examples disclosed herein may be combined or substituted.

In some examples, one or more of the piezoelectric transducers or piezoelectric receiving faces are oriented at an angle of up to five degrees. In some examples, one or more of the piezoelectric transducers or piezoelectric receiving faces are oriented at an angle of up to ten degrees. In some examples, one or more of the piezoelectric transducers or piezoelectric receiving faces are oriented at an angle of up to fifteen degrees. In some examples, one or more of the piezoelectric transducers or piezoelectric receiving faces are oriented at an angle of up to twenty degrees. In some examples, one or more of the piezoelectric transducers or piezoelectric receiving faces are oriented at an angle of greater than twenty degrees.

While IMD 20 is shown in FIG. 1 as being implanted along a portion of the lower leg of the patient and provided for stimulating the tibial nerve of the patient to treat overactive bladder syndrome, IMD 20 could be implanted at numerous sites according to patient need and the particular medical application. In another example, IMD 20 may be implanted to deliver a stimulation therapy to nerves that innervate muscles of the pelvic floor, such as periurethral muscles or the external urethral sphincter for treating symptoms of urinary incontinence or overactive bladder syndrome. In another example, IMD 20 may be implanted to deliver stimulation to the sacral nerve or pudendal nerve to treat overactive bladder syndrome. In other examples, IMD 20 may be deployed for delivering neurostimulation therapy to an acupuncture point for treatment of a symptom associated with the acupuncture point. IMD 20 may be implemented in a system for providing numerous types of neurostimulation therapies, such as for pain control, autonomic nervous system modulation, functional electrical stimulation, tremor, and more.

The embodiments described herein are not limited to a particular size and volume of IMD 20, but are generally implemented to enable the use of a reduced size device for minimally invasive implantation procedures and minimized discomfort to a patient. It is recognized, however, that the various IMD systems described herein may be implemented in conjunction with a wide variety of IMD sizes and volumes adapted for a particular therapy or monitoring application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable medical electrical stimulation device, comprising:
    an electrical stimulation therapy circuit operably coupled to one or more electrodes configured to deliver electrical stimulation therapy;
    a rechargeable battery configured to power the electrical stimulation therapy circuit; and
    an array of piezoelectric transducers, wherein each of the piezoelectric transducers includes a receiving face configured to received transmitted ultrasonic waves convertible to source of electrical energy for selective recharging of the rechargeable battery, wherein the array of piezoelectric transducers are arranged such that at least two of the receiving faces are positioned at an oblique angle to one another to enable receipt of transmitted ultrasonic waves across a wide range of angles, wherein a biocompatible titanium casing includes a domed protrusion configured to focus transmitted ultrasonic waves towards the receiving faces of the array of piezoelectric transducers.

2. The implantable medical electrical stimulation device of claim 1, wherein the array of piezoelectric transducers is configured to receive transmitted ultrasonic waves across a range of about 40 degrees relative to a central poling axis of the array of the piezoelectric transducers.

3. The implantable medical electrical stimulation device of claim 1, wherein the array of piezoelectric transducers is configured to receive transmitted ultrasonic waves in a frequency range of between about 100 kHz and about 5 MHz.

4. The implantable medical electrical stimulation device of claim 1, further comprising a feedback coil configured to generate an indication level of regenerative electrical power received from transmitted ultrasonic waves.

5. The implantable medical electrical stimulation device of claim 1, wherein at least two of the receiving faces are offset about 15 degrees relative to one another.

6. The implantable medical electrical stimulation device of claim 1, wherein the array of piezoelectric transducers includes a central transducer having a receiving face positioned substantially orthogonal to a central poling axis, and a plurality of peripheral transducers, each having a receiving face offset about 15 degrees relative to the receiving face of the central transducer.

7. The implantable medical electrical stimulation device of claim 1, wherein the receiving faces of the array of piezoelectric transducers are covered in an epoxy layer.

8. The implantable medical electrical stimulation device of claim 1, wherein the receiving faces of the array of piezoelectric transducers are covered in the biocompatible titanium casing.

9. The implantable medical electrical stimulation device of claim 1, wherein the domed protrusion is centrally disposed along a generally planar portion of a housing of the implantable medical electrical stimulation device.

10. An implantable medical electrical stimulation device, comprising:
   an electrical stimulation therapy circuit operably coupled to one or more electrodes configured to deliver electrical stimulation therapy;
   a rechargeable battery configured to power the electrical stimulation therapy circuit; and
   an array of piezoelectric transducers, wherein each of the piezoelectric transducers includes a receiving face configured to received transmitted ultrasonic waves convertible to source of electrical energy for selective recharging of the rechargeable battery, wherein the array of piezoelectric transducers are arranged such that at least two of the receiving faces are positioned at an oblique angle to one another to enable receipt of transmitted ultrasonic waves across a wide range of angles, wherein the array of piezoelectric transducers is configured to receive transmitted ultrasonic waves across a range of about 40 degrees relative to a central poling axis of the array of the piezoelectric transducers.

11. An implantable medical electrical stimulation device, comprising:
   an electrical stimulation therapy circuit operably coupled to one or more electrodes configured to deliver electrical stimulation therapy;
   a rechargeable battery configured to power the electrical stimulation therapy circuit; and
   an array of piezoelectric transducers, wherein each of the piezoelectric transducers includes a receiving face configured to received transmitted ultrasonic waves convertible to source of electrical energy for selective recharging of the rechargeable battery, wherein the array of piezoelectric transducers are arranged such that at least two of the receiving faces are positioned at an oblique angle to one another to enable receipt of transmitted ultrasonic waves across a wide range of angles, wherein the array of piezoelectric transducers includes a central transducer having a receiving face positioned substantially orthogonal to a central poling axis, and a plurality of peripheral transducers, each having a receiving face offset about 15 degrees relative to the receiving face of the central transducer.

* * * * *